(12) United States Patent
Bertogg et al.

(10) Patent No.: US 10,556,869 B2
(45) Date of Patent: Feb. 11, 2020

(54) PROCESS FOR THE PRODUCTION OF CONDENSED IMIDAZOLO DERIVATIVES

(71) Applicant: Novartis AG, Basel (CH)

(72) Inventors: Andreas Bertogg, Aarau (CH); Hanspeter Schilling, Bottmingen/BL (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/546,707

(22) PCT Filed: Jan. 28, 2016

(86) PCT No.: PCT/IB2016/050433
§ 371 (c)(1),
(2) Date: Jul. 27, 2017

(87) PCT Pub. No.: WO2016/120821
PCT Pub. Date: Aug. 4, 2016

(65) Prior Publication Data
US 2018/0002292 A1    Jan. 4, 2018

Related U.S. Application Data

(60) Provisional application No. 62/109,307, filed on Jan. 29, 2015.

(51) Int. Cl.
| | |
|---|---|
| C07D 487/00 | (2006.01) |
| C07D 233/54 | (2006.01) |
| A61K 31/4184 | (2006.01) |
| C07D 403/10 | (2006.01) |
| C07D 487/04 | (2006.01) |
| C07D 471/04 | (2006.01) |
| C07D 473/00 | (2006.01) |

(52) U.S. Cl.
CPC ........ *C07D 233/54* (2013.01); *A61K 31/4184* (2013.01); *C07D 403/10* (2013.01); *C07D 487/04* (2013.01)

(58) Field of Classification Search
CPC .......................... C07D 487/04; A61K 31/4184
See application file for complete search history.

(56) References Cited

U.S. PATENT DOCUMENTS 8,314,097 B2 * 11/2012 Ksander ............... C07D 471/04
514/233.2

FOREIGN PATENT DOCUMENTS

| WO | WO2007/024945 A1 | 3/2007 |
| WO | WO2011/088188 A1 | 7/2011 |

OTHER PUBLICATIONS

Meredith et al. (ACS Medicinal Chemistry Letters, 2013, 4, supporting experimental documents, pp. 1-13).*

(Continued)

*Primary Examiner* — Susanna Moore
(74) *Attorney, Agent, or Firm* — Michelle Han

(57) ABSTRACT

The present invention relates to a process for providing the compound of formula I, comprising the step of reacting a compound of formula VII with a base in the presence of an alkaline- or alkaline earth metal salt (MX), wherein LG is a leaving group. The presence of an alkaline- or alkaline earth metal salt was surprisingly found to render said reaction highly reliable in terms of the yield and purity of the compound of formula I obtained. In a further aspect, the present invention relates to the compound of formula I, having less than an amount of 1.50% or less than an amount of 1.25% or less than an amount of 1.00% or less than an amount of 0.75% or less than an amount of 0.50% or less than an amount of 0.25% or less than an amount of 0.10% of the compound of formula VIII.

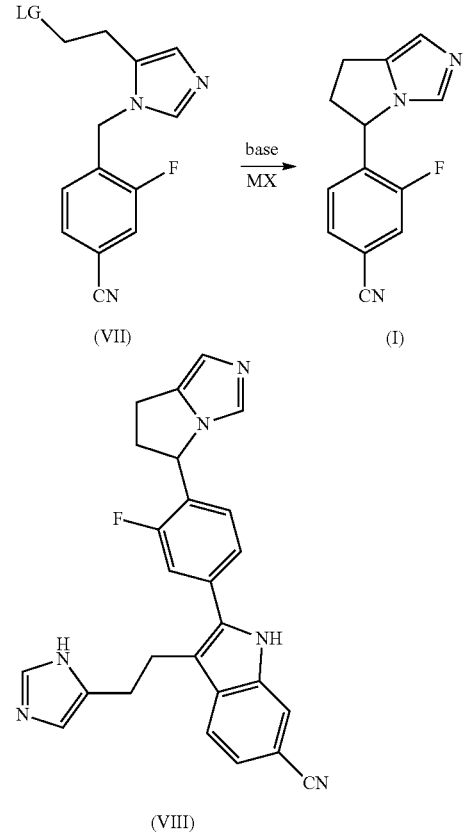

10 Claims, No Drawings

(56) References Cited

OTHER PUBLICATIONS

Meredith et.al., "Discovery and in Vivo Evaluation of Potent Dual CYP11B2 (Aldosterone Synthase) and CYP11B1 Inhibitors", ACS Medicinal Chemistry Letters, vol. 4, pp. 1203-1207, Oct. 17, 2013.
Cerny et al., "Progress Towards Clinically Useful Aldosterone Synthase Inhibitors", Current Topics in Medicinal Chemistry, vol. 13(12), pp. 1385-1401, Jan. 3, 2013.

* cited by examiner

PROCESS FOR THE PRODUCTION OF CONDENSED IMIDAZOLO DERIVATIVES

FIELD OF THE INVENTION

The present invention relates to a novel process for the production of 4-(6,7-dihydro-5H-pyrrolo[1,2-c]imidazole-5-yl)-3-fluorobenzonitrile in free form or in salt form.

BACKGROUND OF THE INVENTION

The compound 4-(6,7-dihydro-5H-pyrrolo[1,2-c]imidazole-5-yl)-3-fluorobenzonitrile of the formula I

(I)

is described in WO2007/024945, WO2011/088188, WO2013/109514 and in E. L. Meredith et al., *ACS Med. Chem. Lett.* 2013, 4, 1203-1207. (R)-4-(6,7-dihydro-5H-pyrrolo[1,2-c]imidazol-5-yl)-3-fluorobenzonitrile of formula Ia can be used as an aldosterone synthase (CYP11B2) inhibitor in the treatment of diseases and disorders characterized by increased stress hormone levels, such as in Cushing's syndrome, Cushing's disease and hypercortisolemia.

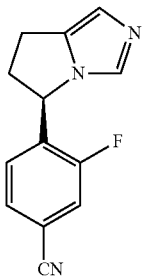

(Ia)

For marketing products, it is necessary to produce pharmaceuticals in large quantities. Hence, short and high-yielding syntheses are of utmost importance.

The compound 4-((5-(2-((tert-butyldimethylsilyl)oxy)ethyl)-1H-imidazol-1-yl)methyl)-3-fluorobenzonitrile of the formula II

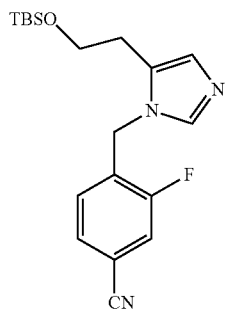

(II)

is a valuable intermediate for the production of 4-(6,7-dihydro-5H-pyrrolo[1,2-c]imidazole-5-yl)-3-fluorobenzonitrile (formula I). Hence, WO2007/024945 and Meredith et al., *ACS Med. Chem. Lett.* 2013, 4, 1203-1207 disclose a process for the production of 4-(6,7-dihydro-5H-pyrrolo[1,2-c]imidazole-5-yl)-3-fluorobenzonitrile (formula I), whereby the benzylic position of the compound of formula II is activated by the installation of an auxiliary ester moiety to give methyl 2-(5-(2-((tert-butyldimethylsilyl)oxy)ethyl)-1H-imidazol-1-yl)-2-(4-cyano-2-fluorophenyl)acetate (formula III).

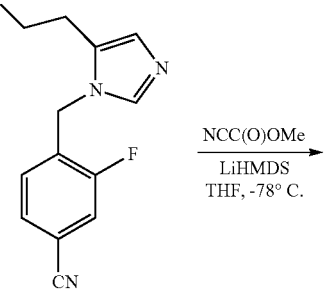

(II)

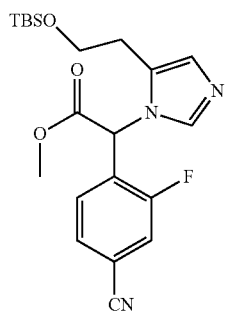

(III)

Subsequent removal of the silyl protecting group from the compound of formula III, followed by mesylation of the resulting primary alcohol yields methyl 2-(4-cyano-2-fluorophenyl)-2-(5-(2-((methylsulfonyl)oxy)ethyl)-1H-imidazol-1-yl)acetate (formula IV), which upon treatment with base undergoes cyclization to afford methyl 5-(4-cyano-2-fluorophenyl)-6,7-dihydro-5H-pyrrolo[1,2-c]imidazole-5-carboxylate (formula V). The compound of formula V is transformed into the compound of formula I by saponification of the methyl ester group followed by decarboxylation.

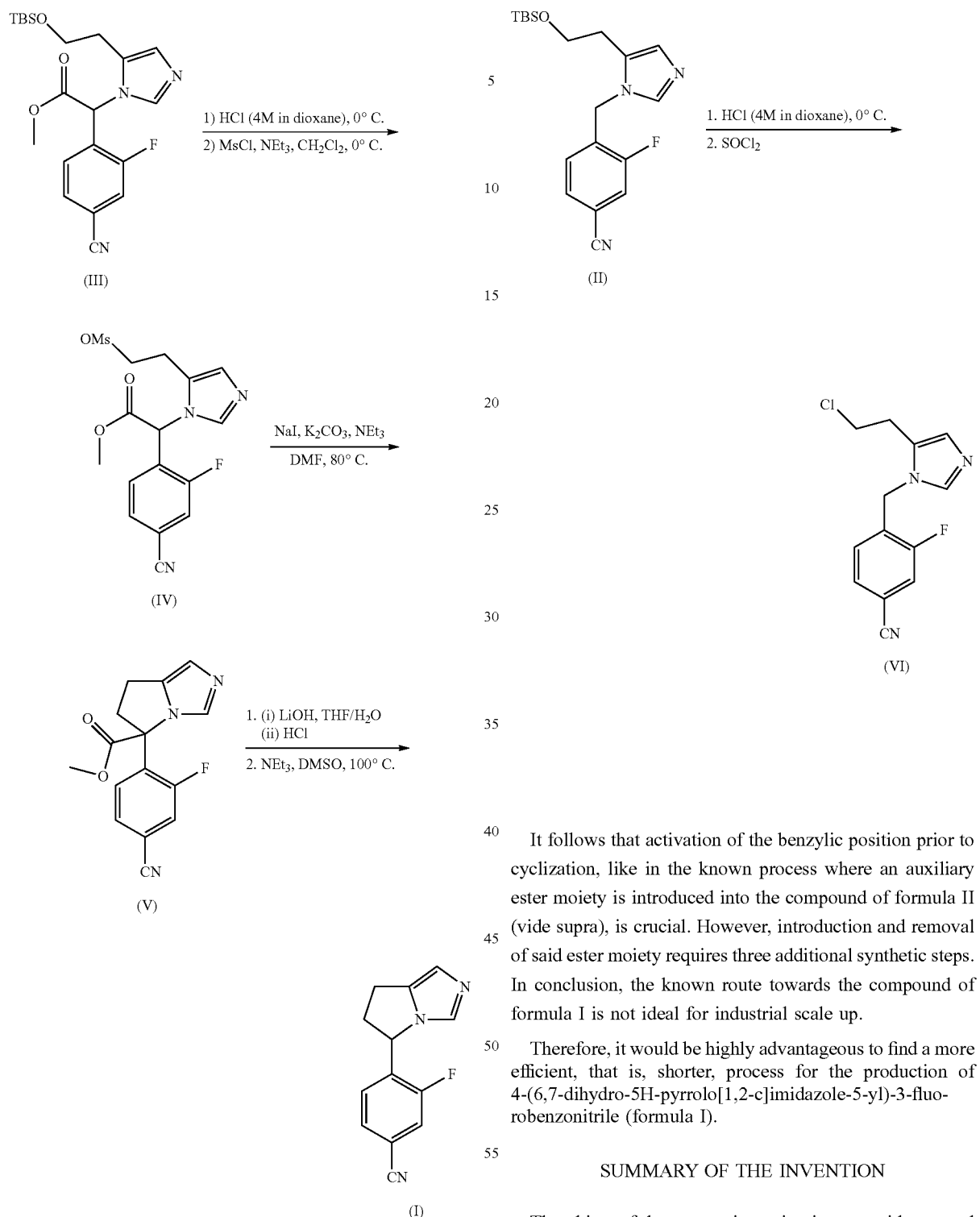

In respect of the synthetic route shown above it is important to note that attempts at cyclizing 4-((5-(2-chloroethyl)-1H-imidazol-1-yl)methyl)-3-fluorobenzonitrile (formula VI) by reacting it with a base, which would constitute a shorter route towards the compound of formula I, resulted in HCl elimination rather than cyclization, as reported by Meredith et al. (*ACS Med. Chem. Lett.* 2013, 4, 1203-1207).

It follows that activation of the benzylic position prior to cyclization, like in the known process where an auxiliary ester moiety is introduced into the compound of formula II (vide supra), is crucial. However, introduction and removal of said ester moiety requires three additional synthetic steps. In conclusion, the known route towards the compound of formula I is not ideal for industrial scale up.

Therefore, it would be highly advantageous to find a more efficient, that is, shorter, process for the production of 4-(6,7-dihydro-5H-pyrrolo[1,2-c]imidazole-5-yl)-3-fluorobenzonitrile (formula I).

SUMMARY OF THE INVENTION

The object of the present invention is to provide a novel process for the production of 4-(6,7-dihydro-5H-pyrrolo[1,2-c]imidazole-5-yl)-3-fluorobenzonitrile (formula I), or a pharmaceutically acceptable salt thereof, which allows it to prepare said compound in high yields and high purity.

The process according to the present invention for producing the compound of formula I or a pharmaceutically acceptable salt thereof, as defined herein, is summarized in Scheme 1.

Scheme 1

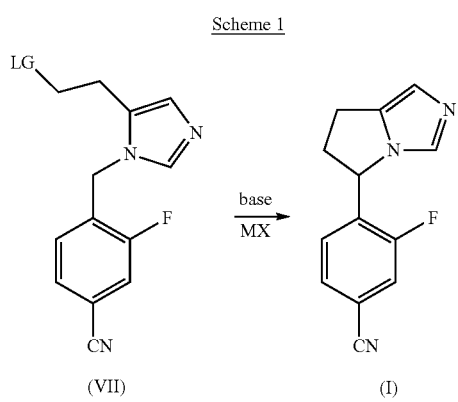

Thus, in accordance with a first aspect of the present invention, there is provided a process for providing the compound of formula I,

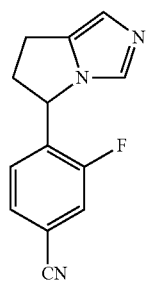
(I)

comprising the step of: (i) reacting a compound of formula VII

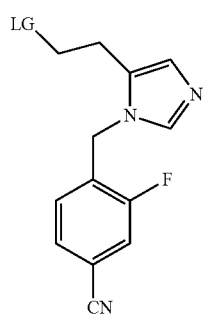
(VII)

with a base in the presence of an alkaline- or alkaline earth metal salt (MX in scheme 1) to form the compound of formula I, wherein LG is a leaving group.

The compound of formula VII may be prepared according to the procedures described in WO2007/024945 and in Meredith et al., *ACS Med. Chem. Lett.* 2013, 4, 1203-1207.

The inventors have discovered surprisingly that the presence of an alkaline- or alkaline earth metal salt suppressed elimination of the leaving group from the compound of formula VII when reacting the compound of formula VII with a base. The inventors have further found that the use of an alkaline- or alkaline earth metal salt suppressed the formation of 3-(2-(1H-imidazol-5-yl)ethyl)-2-(4-(6,7-dihydro-5H-pyrrolo[1,2-c]imidazol-5-yl)-3-fluorophenyl)-1H-indole-6-carbonitrile (formula VIII), which the inventors had commonly observed as a side product when the compound of formula VII was treated with a base in the absence of said alkaline- or alkaline earth metal salt. In this respect it is important to note that the compound of formula VIII was inseparable from the compound of formula I using standard crystallization techniques.

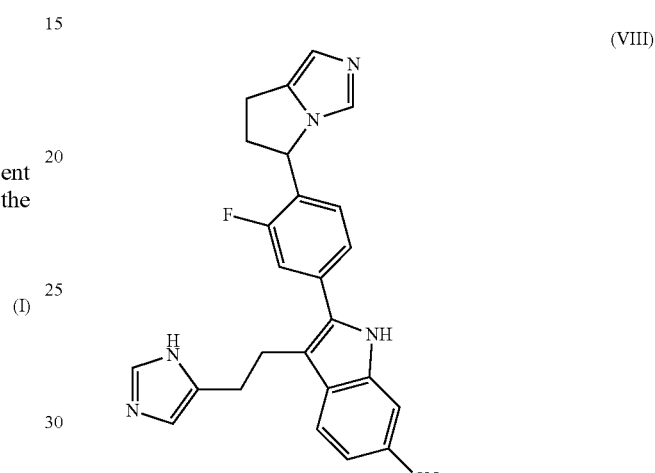
(VIII)

Hence, in a second aspect of the invention, there is provided a compound of formula (I), or one of its enantiomers of formula (Ia) or (Ib), or a pharmaceutically acceptable salt of either one of them, having less than an amount of 1.50% or less than an amount of 1.25% or less than an amount of 1.00% or less than an amount of 0.75% or less than an amount of 0.5% or less than an amount of 0.25% or less than an amount of 0.1% of 3-(2-(1H-imidazol-5-yl)ethyl)-2-(4-(6,7-dihydro-5H-pyrrolo[1,2-c]imidazol-5-yl)-3-fluorophenyl)-1H-indole-6-carbonitrile (formula (VIII)) as byproduct (impurity).

Furthermore, the inventors of the present invention have found that using an alkaline- or alkaline earth metal salt salt in the reaction of the compound of formula VII with a base led to reproducible results with regard to the yield and purity of the compound of formula I obtained from the process. In other words, the process of the present invention is highly reliable, providing the compound of formula I from the compound of formula VII in a single step, in consistently high yields and in high purity.

DETAILED DESCRIPTION OF THE INVENTION

Herein after, the present invention is described in further detail and is exemplified.

In a first aspect of the invention, there is provided a process for providing the compound of formula (I),

(I)

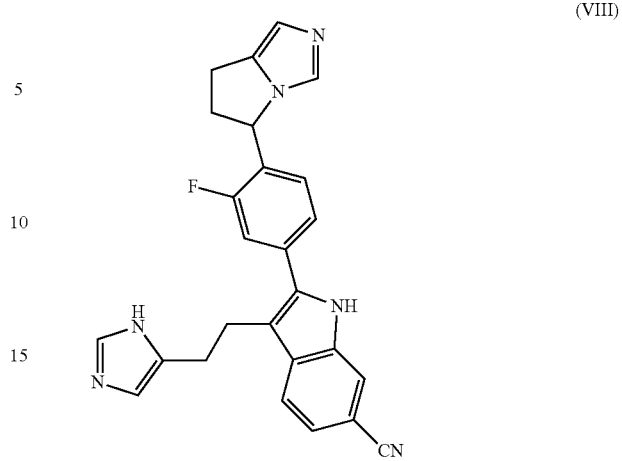

(VIII)

comprising the step of:
(i) reacting a compound of formula VII

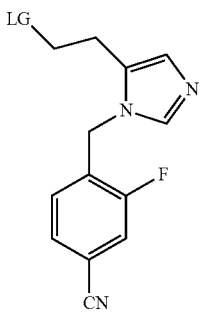

(VII)

with a base in the presence of an alkaline- or alkaline earth metal salt, wherein LG is a leaving group.

In one embodiment, the process according to the invention further comprises a step (ii) of separating the enantiomers of formula (Ia) and (Ib) of the compound of formula (I).

In one embodiment, the process according to the invention further comprises one step of converting the compound of formula I or either one of its enantiomers of formula (Ia) and (Ib) to a pharmaceutically acceptable salt thereof. In one embodiment, said pharmaceutically acceptable salt is the monophosphate salt. In one embodiment, the process of the invention comprises a further step of purifying the compound of formula I or either one of its enantiomers or a pharmaceutically acceptable salt thereof.

In one embodiment, the compound of formula (VIII), being an impurity, is removed by chromatography, for example high pressure liquid chromatography (HPLC).

As pointed out above, the inventors have discovered that the presence of an alkaline- or alkaline earth metal salt suppressed the formation of 3-(2-(1H-imidazol-5-yl)ethyl)-2-(4-(6,7-dihydro-5H-pyrrolo[1,2-c]imidazol-5-yl)-3-fluorophenyl)-1H-indole-6-carbonitrile (formula VIII) when the compound of formula VII was reacted with a base.

Accordingly, in one embodiment of the process of the invention, the compound of formula I as obtained by step (i) of said process contains less than an amount of 1.50% or less than an amount of 1.25% or less than an amount of 1.00% or less than an amount of 0.75% or less than an amount of 0.50% or less than an amount of 0.25% or less than an amount of 0.10% of the compound of formula VIII, wherein said amount of the compound of formula VIII is calculated from an HPLC chromatogram recorded at 275 nm according to the following formula:

% compound of formula $VIII=(A_{VIII}/A_I) \times 100$, wherein $A_{VIII}$ is the peak area corresponding to the compound of formula VIII and $A_I$ is the peak area corresponding to the compound of formula I.

In a further embodiment of the process of the invention, the compound of formula (Ia) as obtained by step (ii) of said process contains less than an amount of 1.50% or less than an amount of 1.25% or less than an amount of 1.00% or less than an amount of 0.75% or less than an amount of 0.50% or less than an amount of 0.25% or less than an amount of 0.10% of the compound of formula VIII, wherein said amount of the compound of formula VIII is calculated from an HPLC chromatogram recorded at 275 nm according to the following formula:

% compound of formula $VIII=(A_{VIII}/A_{Ia}) \times 100$, wherein $A_{VIII}$ is the peak area corresponding to the compound of formula VIII and $A_{Ia}$ is the peak area corresponding to the compound of formula (Ia).

Peaks corresponding to other eventually occurring impurities within the sample being analyzed are not taken into account. It should be noted that the relative peak area as determined using the formula above may vary depending on the HPLC conditions used. In a further embodiment, the compounds of formula I and VIII are being detected using a diode array detector operating at 275 nm. In another embodiment, the sample is prepared by dissolving 0.05% wt/wt of a given mixture of compound of formula I and impurities such as compound of formula VIII in acetonitrile/water (1:1). In a further embodiment, a flow rate of 1.0 mL/min is used at a column temperature of 40° C. Suitable HPLC conditions for the purposes of the present invention are disclosed in Example 1.

In one embodiment, the base according to the process of the invention is selected from the list consisting of
1. an alkaline- or alkaline earth metal alkoxide;
2. an alkaline- or alkaline earth metal amide;
3. an alkaline- or alkaline earth metal hydride;
4. an organolithium reagent; and
5. an organomagnesium reagent.

Examples of alkaline- or alkaline earth metal amide bases are lithium bis(trimethylsilyl)amide, sodium bis(trimethylsilyl)amide or potassium bis(trimethylsilyl)amide. In one embodiment, the base is lithium bis(trimethylsilyl)amide.

Examples of alkaline- or alkaline earth metal alkoxide bases are sodium methoxide, potassium methoxide, lithium methoxide, sodium ethoxide, potassium ethoxide, lithium ethoxide, sodium 2-methylpropan-2-olate, potassium 2-methylpropan-2-olate, lithium 2-methylpropan-2-olate, sodium propan-2-olate, potassium propan-2-olate or lithium propan-2-olate. In one embodiment, the base is potassium 2-methylpropan-2-olate.

In a further embodiment, the base is sodium hydride, potassium hydride or lithium hydride.

In a further embodiment, the base is an organolithium reagent, such as n-butyllithium, sec-butyllithium, tert-butyllithium or phenyllithium.

In a further embodiment, the base is an organomagnesium reagent, such as methylmagnesium chloride, methylmagnesium bromide, methylmagnesium iodide, ethylmagnesium chloride, ethylmagnesium bromide, ethylmagnesium iodide, iso-propylmagnesium chloride, iso-propylmagnesium bromide or iso-propylmagnesium iodide.

In one embodiment, the leaving group according to the process of the invention is a halogenide (halo), a hydroxyl group activated through esterification or cyanide. Halogenide leaving groups are for example fluoride, chloride, bromide or iodide. In a further embodiment, the leaving group is chloride. Examples of hydroxyl groups activated through esterification, which are suitable leaving groups, are sulfonate groups, such as methanesulfonyloxy, toluenesulfonyloxy, fluorosulfonyloxy, trifluoromethanesulfonyloxy or nonabutanesulfonyloxy.

In one embodiment, the alkaline- or alkaline earth metal salt according to the process of the invention is a lithium salt, a sodium salt, a potassium salt, a magnesium salt or a calcium salt.

In a further embodiment, the salt is a lithium halogenide, examples of which are lithium chloride, lithium bromide, lithium iodide, lithium carbonate, lithium sulfate or lithium phosphate. In one embodiment, the lithium salt is lithium bromide.

Examples of sodium salts are sodium halogenides such as sodium chloride, sodium bromide, sodium iodide, sodium carbonate, sodium sulfate or sodium phosphate. In one embodiment, the salt is sodium bromide.

Examples of potassium salts are potassium halogenides, such as potassium chloride, potassium bromide, potassium iodide, potassium carbonate, potassium sulfate and potassium phosphate. In one embodiment, the salt is potassium bromide.

Examples of magnesium salts are magnesium halogenides, such as magnesium chloride, magnesium bromide, magnesium iodide, magnesium carbonate, magnesium sulfate and magnesium phosphate. In one embodiment, the salt is magnesium bromide.

Examples of calcium salts are calcium halogenides, such as calcium chloride, calcium bromide, calcium iodide, calcium carbonate, calcium sulfate and calcium phosphate. In one embodiment, the salt is calcium bromide.

In one embodiment, the base according to the invention is an anionic base, wherein the counter ion is identical to the cation present in the alkaline- or alkaline earth metal salt according to the process of the invention. Hence, where for example lithium bis(trimethylsilyl)amide is used as the base according to the process of the invention, a lithium salt, such as lithium chloride or lithium bromide, is used as the salt according to the process of the invention.

In one embodiment, the base according to the invention is an anionic base, wherein the counter ion is different from the cation present in the alkaline- or alkaline earth metal salt according to the process of the invention. Hence, where for example sodium bis(trimethylsilyl)amide is used as the base according to the process of the invention, a lithium salt, such as lithium chloride or lithium bromide, is used as the salt according to the process of the invention.

In a further embodiment, the process according to the invention is carried out in solution. For example, the solvent is an aprotic solvent which is inert to the reaction conditions.

In one embodiment, the process according to the present invention is carried out in an ether solvent. The term ether as used herein refers to a compound of the formula ROR', wherein R and R' are independently of each other alkyl, aryl, arylalkyl, cycloalkyl, alkenyl or alkoxyalkyl; or R and R' combined are an alkylene, alkenylene or alkoxyalkylene, which together with the oxygen atom to which they are attached form a 5- to 8-membered ring. Examples of ethers are tetrahydrofuran, tetrahydropyran, oxepane, oxocane, dimethyl ether, diethyl ether, methoxyethane, 2-isopropoxypropane, 2-methoxy-2-methylpropane or dioxane. In one embodiment, the ether solvent is tetrahydrofuran.

In one embodiment, the process according to the present invention is carried out in an ether solvent of the formula ROR', wherein R and R' combined are an alkylene, alkenylene or alkoxyalkylene, which together with the oxygen atom to which they are attached form a 5- to 8-membered ring.

The term alkyl as used herein refers to a radical or part of a radical which is a straight or branched (one or, if desired and possible, more times) carbon chain, and is especially $C_1$-$C_7$-alkyl, such as $C_1$-$C_4$-alkyl, in particular branched $C_1$-$C_4$-alkyl, such as isopropyl. The term "$C_1$-$C_7$-" defines a moiety with up to and including maximally 7, especially up to and including maximally 4, carbon atoms, said moiety being branched (one or more times) or straight-chained and bound via a terminal or a non-terminal carbon. $C_1$-$C_7$-alkyl, for example, is n-pentyl, n-hexyl or n-heptyl or preferably $C_1$-$C_4$-alkyl, especially as methyl, ethyl, n-propyl, iso-propyl, n-butyl, isobutyl, sec-butyl, tert-butyl, in particular methyl, ethyl, n-propyl, iso-propyl, n-butyl, isobutyl, sec-butyl or tert-butyl.

The term alkenyl as used herein refers to a radical or part of a radical which is a straight or branched (one or, if desired and possible, more times) carbon chain containing at least one double bond, and includes, for example, $C_2$-$C_{20}$-alkenyl (such as $C_3$-$C_8$-alkenyl). Examples include ethenyl and the isomers of propyl, butyl, pentyl, hexyl, heptyl, octyl, nonyl, decyl, undecyl, dodecyl, tetradecyl, hexadecyl, octacyl and eicosyl, each of which containing at least one double bond.

The term cycloalkyl as used herein refers to a radical or part of a radical which includes "$C_3$-$C_8$-cycloalkyl" and defines a non-aromatic cycloalkyl moiety with up to and including maximally 14, such as up to and including 10, for example up to and including maximally 8, in particular up to and including maximally 6 carbon atoms. Said cycloalkyl moiety is for example mono- or bicyclic, in particular monocyclic, which may include one or more double and/or triple bonds. Embodiments include cyclopropyl, cyclobutyl, cyclopentyl, cyclohexyl, cycloheptyl or cyclooctyl.

The term alkoxy, being a radical or part of a radical, refers to alkyl-O—, wherein the term alkyl is as defined herein, and includes, for example, $C_1$-$C_{20}$-alkoxy (—O—$C_1$-$C_{20}$-alkyl), preferably $C_1$-$C_7$-alkoxy (—O—$C_1$-$C_7$-alkyl). In particular, alkoxy includes, for example, methoxy, ethoxy, n-propyloxy, isopropyloxy, n-butyloxy, isobutyloxy, sec-butyloxy, tert-butyloxy, pentyloxy, hexyloxy or heptyloxy radicals.

Alkoxyalkyl may be linear or branched. The alkoxy group may for example comprise 1 to 7 and in particular 1 to 4 C atoms, and the alkyl group for example may comprise 1 to 7 and in particular 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxy-propyl, 4-ethoxybutyl, 5-ethoxypentyl, 6-ethoxyhexyl, propyloxymethyl, butyloxymethyl, 2-propyloxyethyl and 2-butyloxyethyl.

The term aryl as used herein, being a radical or part of a radical, refers to an aromatic hydro-carbon group, for example, $C_{6-10}$-aryl, and is preferably a mono- or polycyclic, especially monocyclic, bicyclic or tricyclic aryl moiety with 6 to 14 carbon atoms for example 6 to 10 carbon atoms, preferably phenyl, indenyl, indanyl or naphthyl.

The term arylalkyl includes aryl-$C_1$-$C_7$-alkyl, preferably aryl-$C_1$-$C_4$-alkyl, wherein aryl is as defined herein and is for example benzyl.

The term alkylene as used herein refers to a bivalent radical derived from alkyl and includes $C_1$-$C_7$-alkylene, preferably $C_2$-$C_4$-alkylene.

The term alkenylene as used herein refers to a bivalent radical derived from alkenyl, including in particular $C_{2-7}$ alkenylene, preferably $C_2$-$C_4$-alkenylene.

The term alkoxyalkylene as used herein refers to a bivalent radical derived from alkoxyalkyl, including in particular $C_{2-7}$-alkoxyalkyl, preferably $C_2$-$C_4$-alkoxyalkyl.

In a further embodiment of the process according to the present the invention, the reaction is carried out in a solvent being an N,N-dialkyl amide, preferably N,N-dimethylformamide, or a dialkyl sulfoxide, preferably dimethyl sulfoxide, or a nitrile, preferably benzonitrile or acetonitrile.

In one embodiment of the process according to the present invention, the reaction is carried out at a temperature of −100° C. to 0° C. or −100° C. to −10° C. or −90° C. to −10° C. or −80° C. to −20° C. or −70° C. to −20° C. or −60° C. to −20° C. or −50° C. to −20° C. or −40° C. to −20° C. or −30° C. to −20° C. Preferably, the reaction is carried out at a temperature of −50° C. to −25° C.

In one embodiment of the process according to the present invention, 0.5 to 5 equivalents of base are used relative to the compound of formula VII. Alternatively, 0.5 to 4.5 or 0.5 to 4.0 or 0.5 to 3.5 or 0.5 to 3.0 or 0.5 to 2.5 or 0.5 to 2.0 or 0.5 to 1.5 equivalents of base are used relative to the compound of formula VII. In a further embodiment, 0.8 to 1.3 equivalents of base are used relative to the compound of formula VII. It should be noted that excess base is likely to lead to the formation of side products.

In one embodiment of the process according to the present invention, 0.1 to 5 equivalents of the alkaline- or alkaline earth metal salt are used relative to the compound of formula VII. Alternatively, 0.1 to 4.5 or 0.1 to 4.0 or 0.1 to 3.5 or 0.1 to 3.0 or 0.1 to 2.5 or 0.1 to 2.0 or 0.1 to 1.5 or 0.1 to 1.0 or 0.1 to 0.5 equivalents of the alkaline- or alkaline earth metal salt are used relative to the compound of formula VII. In a further embodiment, 1.5 to 2.5 equivalents of the alkaline- or alkaline earth metal salt are used relative to the compound of formula VII.

In one embodiment of the process according to the present invention, the reaction is stopped after 2 to 15 hours. In a further embodiment, the reaction is stopped after 3 to 6 hours.

In one embodiment of the process according to the invention, the base is selected from the list consisting of
1. an alkaline- or alkaline earth metal alkoxide;
2. an alkaline- or alkaline earth metal amide;
3. an alkaline- or alkaline earth metal hydride;
4. an organolithium reagent; and
5. an organomagnesium reagent and the alkaline- or alkaline earth metal salt is a lithium salt, a sodium salt, a potassium salt, a magnesium salt or a calcium salt.

In one embodiment of the process according to the invention, the base is selected from the list consisting of
1. an alkaline- or alkaline earth metal alkoxide;
2. an alkaline- or alkaline earth metal amide;
3. an alkaline- or alkaline earth metal hydride;
4. an organolithium reagent; and
5. an organomagnesium reagent and the alkaline- or alkaline earth metal salt is a lithium salt, a sodium salt, a potassium salt, a magnesium salt or a calcium salt and the reaction is carried out in a polar, aprotic solvent selected from the list consisting of
1. an ether;
2. an N,N-dialkyl amide; and
3. a dialkyl sulfoxide.

In one embodiment of the process according to the invention, the base is selected from the list consisting of
1. an alkaline- or alkaline earth metal alkoxide;
2. an alkaline- or alkaline earth metal amide;
3. an alkaline- or alkaline earth metal hydride;
4. an organolithium reagent; and
5. an organomagnesium reagent and the alkaline- or alkaline earth metal salt is a lithium halogenide, a sodium halogenide, a potassium halogenide, a magnesium halogenide or a calcium halogenide and the reaction is carried out in a polar, aprotic solvent selected from the list consisting of
1. an ether;
2. an N,N-dialkyl amide; and
3. a dialkyl sulfoxide, at a temperature of −100° C. to 0° C. and 0.5 to 5 equivalents of base are used relative to the compound of formula VII and 0.5 to 5 equivalents of the alkaline- or alkaline earth metal salt are used relative to the compound of formula VII and the reaction is stopped after 2 to 15 hours.

In one embodiment of the process according to the invention, the base is an alkaline- or alkaline earth metal amide and the salt is a lithium halogenide and the reaction is carried out in a solvent being an ether.

In one embodiment of the process according to the invention, the base is an alkaline- or alkaline earth metal amide and the salt is a lithium halogenide and the reaction is carried out in a solvent being an ether of the formula ROR', R and R' combined being an alkylene, alkenylene or alkoxyalkylene, which together with the oxygen atom to which they are attached form a 5- to 8-membered ring.

In one embodiment of the process according to the invention, the base is an alkaline- or alkaline earth metal amide and the salt is a lithium halogenide and the reaction is carried out in a solvent being an ether at a temperature of −100° C. to 0° C. and 0.5 to 5 equivalents of base are used relative to the compound of formula VII and 0.5 to 5 equivalents of the alkaline- or alkaline earth metal salt are used relative to the compound of formula VII and the reaction is stopped after 2 to 15 hours.

In one embodiment of the process according to the invention, the base is an alkaline- or alkaline earth metal amide and the salt is a lithium halogenide and reaction is carried out in a solvent being an ether at a temperature of −50° C. to −25° C. and 0.8 to 1.3 equivalents of base are used relative to the compound of formula VII and 1.5 to 2.5 equivalents of the alkaline- or alkaline earth metal salt are used relative to the compound of formula VII and the reaction is stopped after 3 to 6 hours, the compound of formula (I) as obtained by step (i) of said process having less than an amount of 0.25% or less than an amount of 0.10% of the compound of formula (VIII).

In one embodiment of the process according to the present invention, the base is lithium bis(trimethylsilyl)amide, and the leaving group is chloride, and the alkaline- or alkaline earth metal salt is lithium bromide and the reaction is carried out in tetrahydrofurane at a temperature of −50° C. to −25° C. and 0.8 to 1.3 equivalents of lithium bis(trimethylsilyl) amide are used relative to the compound of formula VII and 1.5 to 2.5 equivalents of lithium bromide are used relative to the compound of formula VII and the reaction is stopped after 3 to 6 hours.

In one embodiment of the process according to the present invention, the base is lithium bis(trimethylsilyl)amide, and the leaving group is chloride, and the alkaline- or alkaline earth metal salt is lithium bromide. In a further embodiment, the reaction is carried out in tetrahydrofurane.

In a further embodiment of the process according to the present invention, the base is lithium bis(trimethylsilyl) amide, and the leaving group is chloride, and the alkaline- or alkaline earth metal salt is lithium bromide and the reaction is carried out in tetrahydrofurane at a temperature of −50° C. to −25° C. and 0.8 to 1.3 equivalents of lithium bis(trimethylsilyl)amide are used relative to the compound of formula VII and 1.5 to 2.5 equivalents of lithium bromide are used relative to the compound of formula VII and the reaction is stopped after 3 to 6 hours, the compound of formula (I) as obtained by step (i) of said process having less than an amount of 1.50% or 1.00% or 0.75% or 0.50% or 0.25% or 0.10% of the compound of formula (VIII).

In a second aspect of the invention, there is provided the compound of formula (I), or one of its enantiomers of formula (Ia) or (Ib), or a pharmaceutically acceptable salt of either one of them, having less than an amount of 1.50% or 1.25% or 1.00% or 0.75% or 0.50% or 0.25% or 0.10% of 3-(2-(1H-imidazol-5-yl)ethyl)-2-(4-(6,7-dihydro-5H-pyrrolo[1,2-c]imidazol-5-yl)-3-fluorophenyl)-1H-indole-6-carbonitrile (formula (VIII)).

In one aspect, there is provided a pharmaceutical composition comprising the substantially pure compound of formula (I) of the invention or a pharmaceutically acceptable salt thereof.

In one aspect, there is provided a pharmaceutical composition comprising the substantially pure compound of formula (Ia) of the invention or a pharmaceutically acceptable salt thereof.

Where an "aspect" is referred to, throughout the present specification this refers to an aspect of the invention if not indicated otherwise.

The term "substantially pure" as used herein means that the compound formula I or the compound of formula (Ia), respectively contains less than an amount of 1.5% or less than an amount of 1.25% or less than an amount of 1.00% or less than an amount of 0.75% or less than an amount of 0.50% or less than an amount of 0.25% or less than an amount of 0.10% of the compound of formula VIII. Said amount of the compound of formula VIII is calculated from an HPLC chromatogram recorded at 275 nm, according to the following formula:

% compound of formula $VIII=(A_{VII}/A_I) \times 100$ or

% compound of formula $VIII=(A_{VIII}/A_{Ia}) \times 100$, wherein $A_{VIII}$ is the peak area corresponding to the compound of formula VIII and $A_{VIII}$ or $A_{Ia}$ is the peak area corresponding to the compound of formula I or compound of formula (Ia).

Another embodiment of the present invention is directed to a pharmaceutical composition comprising (a) a therapeutically effective amount of the substantially pure compound of formula I or one of its enantiomers of formula (Ia) or (Ib), or a pharmaceutically acceptable salt of either one of them, as obtained from the process of the present invention; and (b) at least one pharmaceutically acceptable carrier, diluent, vehicle or excipient. One embodiment is directed at the pharmaceutical compositions as disclosed herein for use as medicaments.

In one embodiment, there is provided a pharmaceutical composition comprising (a) a therapeutically effective amount of the substantially pure compound of formula (Ia) or a pharmaceutically acceptable salt thereof, as obtained from the process of the present invention; and (b) at least one pharmaceutically acceptable carrier, diluent, vehicle or excipient. One embodiment is directed at the pharmaceutical compositions as disclosed herein for use as medicaments.

In a further embodiment, the pharmaceutical compositions disclosed herein are used in the treatment of a disease or disorder characterised by increased stress hormone levels and/or decreased androgen hormone levels in a subject.

In one aspect, the present invention is directed to a process of providing the pharmaceutical compositions as disclosed herein, comprising the step of admixing a therapeutically active amount of the substantially pure compound formula I or one of its enantiomers of formula (Ia), or a pharmaceutically acceptable salt of either one of them, as obtained by the process of the invention, with at least one pharmaceutically acceptable carrier, diluent, vehicle or excipient.

In one aspect, the present invention provides a method of treating a disease or disorder characterised by increased stress hormone levels and/or decreased androgen hormone levels in a subject, comprising administering to the subject a therapeutically effective amount of the substantially pure compound of formula I or one of its enantiomers of formula (Ia) or (Ib), or a pharmaceutically acceptable salt of either one of them, as obtained from the process of the invention.

In one aspect, there is provided a method of treating heart failure, cachexia, acute coronary syndrome, chronic stress syndrome, Cushing's syndrome or metabolic syndrome, comprising administering to the subject a therapeutically effective amount of the substantially pure compound of formula (I) or one of its enantiomers of formula (Ia) or (Ib), or a pharmaceutically acceptable salt of either one of them, as obtained according to the process of the invention.

In one aspect, there is provided the use of the substantially pure compound of formula (I) or one of its enantiomers of formula (Ia) or (Ib), or a pharmaceutically acceptable salt of either one of them, as obtained according to the process of the invention, for the preparation of a pharmaceutical composition for the treatment of a disorder or disease characterised by increased stress hormone levels and/or decreased androgen hormone levels in a subject.

In one aspect, there is provided the use of the substantially pure compound of formula I or one of its enantiomers of formula (Ia) or (Ib), or a pharmaceutically acceptable salt of either one of them, as obtained according to the process of the invention, in the treatment of a disorder or disease characterised by increased stress hormone levels and/or decreased androgen hormone levels in a subject.

In one aspect, the present invention provides the use of the substantially pure compound of formula I or one of its enantiomers of formula (Ia) or (Ib), or a pharmaceutically acceptable salt of either one of them, as obtained according to the process of the invention, for the preparation of a pharmaceutical composition for the treatment of a disorder or disease selected from heart failure, cachexia, acute coronary syndrome, chronic stress syndrome, cushing's syndrome or metabolic syndrome.

In one aspect, there is provided the use of the substantially pure compound of formula I or one of its enantiomers of formula (Ia) or (Ib), or a pharmaceutically acceptable salt of either one of them, as obtained according to the process of the invention, in the treatment of a disorder or disease selected from Cushing's syndrome, Cushing's disease and hypercortisolemia.

A "therapeutically effective amount" is intended to mean the amount of the compound of formula I that, when administered to a subject in need thereof, will elicit a biological or medical response in said subject or ameliorate symptoms, slow or delay disease progression, or prevent a disease etc. The amount of the compound of formula I that will be therapeutically effective will vary depending upon factors such as the disease condition and the severity thereof, the identity of the subject in need thereof, etc., which amount may be routinely determined by artisans of ordinary skill in the art.

A pharmaceutical composition comprising a compound of the formula I, especially Ia, may be prepared according to methods known in the art. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

The pharmaceutical composition according to the present invention can be in unit dosage of at least 0.05 or 1 mg or greater of the compounds described herein as the active ingredient, such as of from 0.01 mg to 1000 mg, of from 0.01 mg to 500 mg, of from 0.01 to 50 mg, of from 0.01 mg to 5 mg, of from 0.01 to 2 mg or of from 0.1 mg to 2 mg of active ingredient; such as in unit dosage of at least 0.05 or 1 mg or of from 4 mg to 100 mg, for example of from 2 mg to 50 mg, of the compounds described herein as the active ingredient for a subject of about 50-70 kg. For example, the unit dosage can contain 1-1000 mg of active ingredient for a subject of about 50-70 kg, about 1-500 mg, about 1-50 mg, about 0.5-5 mg, 0.1-1 mg or about 0.05-0.5 mg of active ingredient. The dosage regimen utilizing the compounds described herein can be selected in accordance with a variety of factors including type, species, age, weight, sex, the type of disease or disorder to be treated, the severity of the disease or disorder to be treated, the route of administration, and the particular compound or salt employed. A physician, clinician or veterinarian of ordinary skill can readily determine the effective amount of each of the active ingredients necessary to prevent, treat or inhibit the progress of the disorder or disease.

Stopping the reaction in the context of the present description means deactivating any unreacted reagents especially by pouring the reaction mixture into water, or into an aqueous solution of a salt like sodium chloride (NaCl) or ammonium chloride ($NH_4Cl$). Preferably, the reaction is stopped by pouring it into a saturated aqueous solution of $NH_4Cl$.

Pharmaceutically acceptable salts of the compound of formula I are formed, for example, as acid addition salts, preferably with organic or inorganic acids. Suitable inorganic acids are, for example, halogenide acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, tartaric acid, amino acids, such as glutamic acid or aspartic acid, maleic acid, hydroxymaleic acid, methylmaleic acid, benzoic acid, methane- or ethane sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In one embodiment of the present invention, the compound of formula I or either one of its enantiomers of formula (Ia) or (Ib) are converted into their monophosphate salts.

For isolation or purification purposes of the compound of formula I, it is also possible to use pharmaceutically unacceptable salts, for example picrates or perchlorates.

The term "chiral" refers to molecules which have the property of non-superimposability on their mirror image partner, while the term "achiral" refers to molecules which are superimposable on their mirror image partner.

The present invention contemplates the compound of formula (I) to include (R)-4-(6,7-dihydro-5H-pyrrolo[1,2-c]imidazol-5-yl)-3-fluorobenzonitrile (formula (Ia)) and (S)-4-(6,7-dihydro-5H-pyrrolo[1,2-c]imidazol-5-yl)-3-fluorobenzonitrile (formula (Ib)).

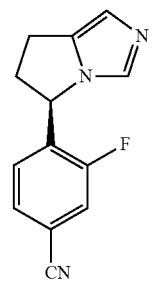

(Ia)

-continued

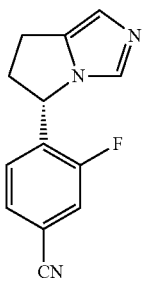
(Ib)

Any resulting mixtures of isomers can be separated on the basis of the physicochemical differences of the constituents, into the pure geometric or optical isomers, for example by chromatography and/or fractional crystallization. Hence, any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The term "$t_r$" as used herein refers to "retention time".

EXAMPLES

Hereinafter, the present invention is illustrated with reference to the following examples, which however do not limit the scope of the present invention.

Example 1

The process was carried out in a dry reactor (rinsed with THF and dried at 85° C.). The compound of formula VI (40.0 kg, 152 mol, 1.00 eq) was dissolved in tetrahydrofuran (140 L) at 20-25° C., then a solution of LiBr was added (87.8 kg of 30% w/w in THF, 303 mol, 1.99 eq) at the same temperature and the resulting mixture was cooled to −30±3° C. Next, a solution of lithium bis(trimethylsilyl)amide (97.5 kg of 24% w/w in THF, 140 mol, 0.92 eq) was added over 2 h, maintaining the temperature at −30±3° C. The mixture was stirred for another 1 h at −30±3° C., whereafter the conversion was assessed by HPLC. Additional LiHMDS may be added in order to achieve full conversion, whereby it was crucial not to exceed a total of 1.00 eq. Finally, the reaction was quenched into pre-cooled (−10° C.) aqueous $NH_4Cl$ (50.3 kg $NH_4Cl$ in 235 L $H_2O$), whereby the temperature was maintained below 0° C. The mixture was then allowed to warm to 20° C. and the layers were separated. The organic phase (532 kg) was concentrated under reduced pressure (450 mbar) and the crude product was used for further steps without purification.

Typical HPLC (column: Waters XBridge C18, particle size: 3.5 μm, dimensions: 150×3.00 mm; detection: diode array detector at 275 nm; flow rate: 1.0 mL/min; column temp.: 40° C.; injection vol.: 10 μL; mobile phase A: 50 mM $NH_4OAc$ in $H_2O$ adjusted to pH 5.6 using AcOH; mobile phase B: acetonitrile; gradient: 0 min 5% mobile phase B, 11 min 55% mobile phase B, 15 min 95% mobile phase B; sample preparation: 0.05% wt/wt in acetonitrile/water 1:1):

$t_{r,1}$=6.40 min (compound of formula I, 93.6%); $t_{r,2}$=8.81 min (compound of formula VI, 4.11%); $t_{r,3}$=8.35 min (compound of formula VIII, 0.03%).

Example 2

(compound of formula Ia; transformation of precursor C5 into precursor C6: The amount (a-%) of precuros 6 C6 shall be maximized while the amounts (a-%) of the side products Q1 and Q2 shall be minimized. The amount of Q1 shall be kept below 0.23 a-%. The yield of C7 (transformation: C5 to C6 to C7) shall be maximized.

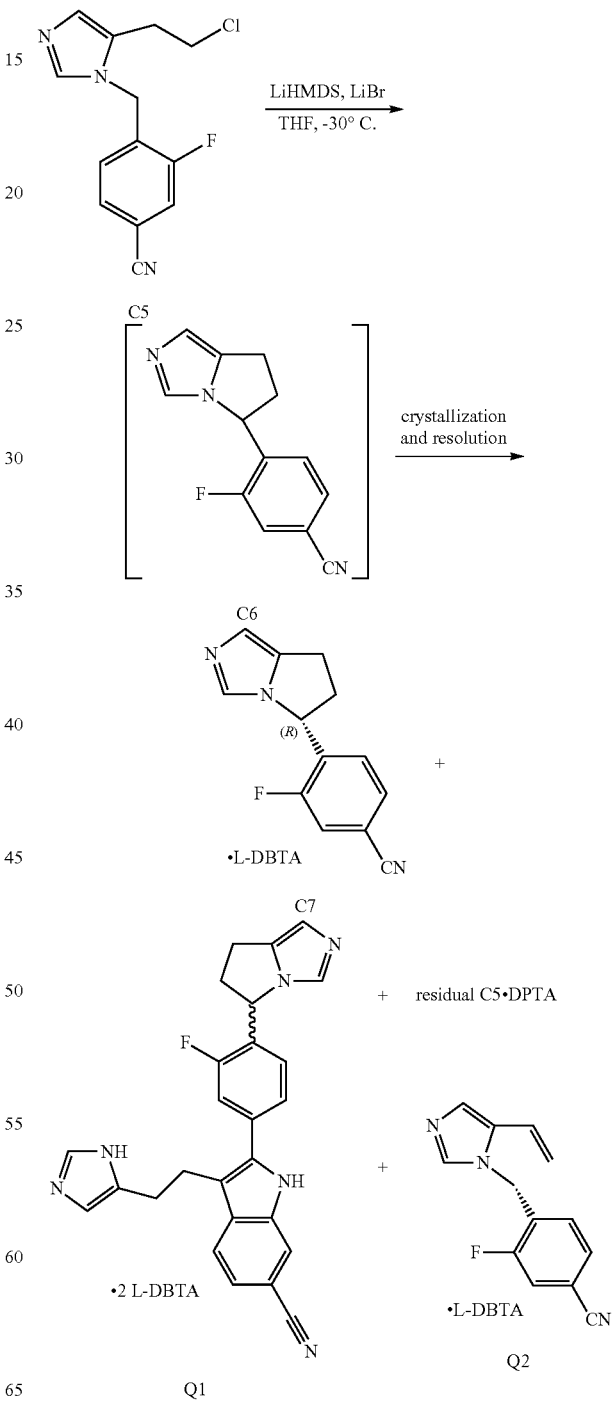

TABLE 1 use of LiBr/variation of the parameters 'equivalents of LiHMDS', 'temperature' and 'reaction time'

| entry | Process | LiBr [eq] | LiHMDS [eq] | addition mode of LiHMDS | T [° C.] | t [h] | C6 [a-%] | C5 [a-%] | Q1 [a-%] | Q2 [a-%] | yield C7 [%] |
|---|---|---|---|---|---|---|---|---|---|---|---|
| 1 | A | 2.00 | 0.95 | LiHMDS to C5 | −43 | 5 | 89.65 | 7.88 | 0.01 | 0.45 | 40 |
| 2 | A | 2.00 | 0.95 | LiHMDS to C5 | −43 | 15 | 89.06 | 7.52 | 0.03 | 0.46 | 42 |
| 3 | A | 2.00 | 0.95 | LiHMDS to C5 | −30 | 4 | 93.58 | 4.11 | 0.03 | 0.41 | 44 |
| 4 | A | 2.00 | 0.95 | LiHMDS to C5 | −30 | 15 | 93.67 | 4.59 | 0.00 | 0.35 | 41 |
| 5 | B | — | 3.50 | C5 to LiHMDS | −43 | 3 | 72.31 | 14.6 | 0.28 | 3.88 | 32 |
| 6 | B | — | 3.50 | C5 to LiHMDS | −43 | 4 | 76.80 | 8.48 | 0.44 | 4.25 | 33 |
| 7 | B | — | 3.50 | C5 to LiHMDS | −43 | 8 | 83.27 | 0.57 | 1.56 | 5.35 | 34 |

The yield of C6 can not be measured since it is not isolated. Therefore the material is further converted to C7 and the yield of C7 is determined.

The aim of this table is to show the influence of LiBr on the transformation C5 to C6. The two processes are defined as follows. In process A, a solution of LiHMDS (0.95 equivalents) in THF is added to a solution of C5 and LiBr in THF at temperature T, stirred for time t, quenched and analyzed by HPLC. In process B, a solution of C5 in THF is added to a solution of LiHMDS (3.50 equivalents) in THF at temperature T, stirred for time t, quenched and analyzed by HPLC. In either case, the intermediate C6 is then transformed into C7 of which the yield is determined. The reaction parameters mentioned above, the results of HPLC analyses and the yields of C7 are summarized in Table 1.

CONCLUSIONS a) Process B (no LiBr used): the transformation of C5 into C6 progresses steadily with increasing time (Table 1, entries 5-7; reaction times 3,4 and 8 h). The amount of Q1 and Q2 increase steadily with time as well. Process B is intrinsically unstable and therefore is not suitable for chemical production.

b) Process A (use of LiBr): the starting material C5 is converted into C6 within 4 h (Table 1, entry 3). There is no measurable increase of Q1 and Q2 with increasing reaction time: even very long reaction times (15 h) lead to low levels of Q1 and Q2 (Table 1, entries 2 & 4). There is no trade-off between conversion and purity: both high conversions and high purities can be achieved over a wide range of reaction times. The reaction is intrinsically stable and suitable for chemical production. The amounts of Q1 and Q2 are significantly lower as compared to the amounts of Q1 and Q2 found in the product of process B.

The invention claimed is:

1. A process for providing a compound of formula (I),

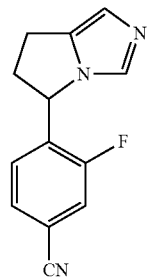

(I)

comprising the step of:
(i) reacting a compound of formula VII

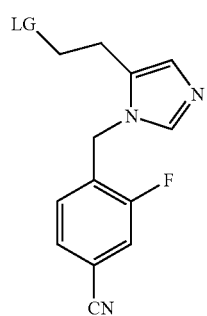

(VII)

with a base, which is lithium bis(trimethylsilyl)amide, in the presence of a lithium halide, wherein LG is a leaving group, and wherein the process is carried out at a temperature of −100° C. to 0° C.

2. A process for providing compounds of formula (Ia) and (Ib), comprising the step of:

(i) reacting a compound of formula VII

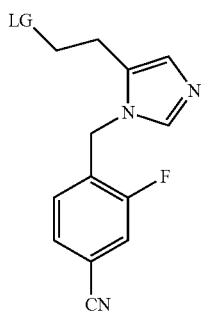
(VII)

with a base, which is lithium bis(trimethylsilyl)amide, in the presence of a lithium halide, wherein LG is a leaving group, wherein the process is carried out at a temperature of −100° C. to 0° C.; and
  (ii) separating the enantiomers of the compound of formula (I), said enantiomers being represented by formula (Ia) and formula (Ib).

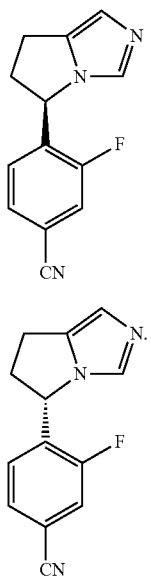
(Ia)

(Ib)

3. The process according to claim 1 or claim 2, wherein the leaving group is a halogen, a hydroxyl group activated through esterification or cyanide.

4. The process according to claim 3, wherein the leaving group is chloride.

5. The process according to claim 1 or claim 2, wherein the process is carried out in an aprotic, inert solvent.

6. The process according to claim 5, wherein the aprotic, inert solvent is tetrahydrofuran.

7. The process according to claim 1 or claim 2, wherein the process is carried out at a temperature of −50° C. to −25° C.

8. The process according to claim 1 or claim 2, wherein 0.5 to 5 equivalents of base are used relative to the compound of formula VII.

9. A process for providing a pharmaceutically acceptable salt of compounds of formula (Ia) and (Ib), comprising the step of:
  (i) reacting a compound of formula VII

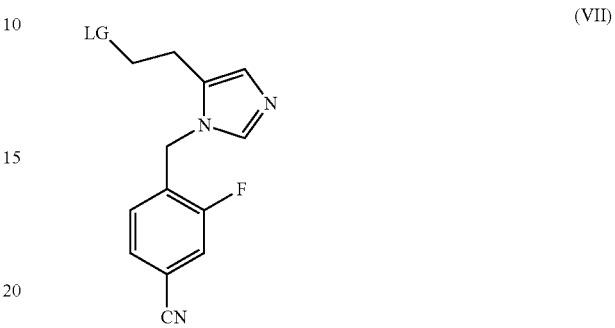
(VII)

with a base, which is lithium bis(trimethylsilyl)amide, in the presence of a lithium halide, wherein LG is a leaving group, wherein the process is carried out at a temperature of −100° C. to 0° C.; and
  (ii) separating the enantiomers of the compound of formula (I), said enantiomers being represented by formula (Ia) and formula (Ib) and

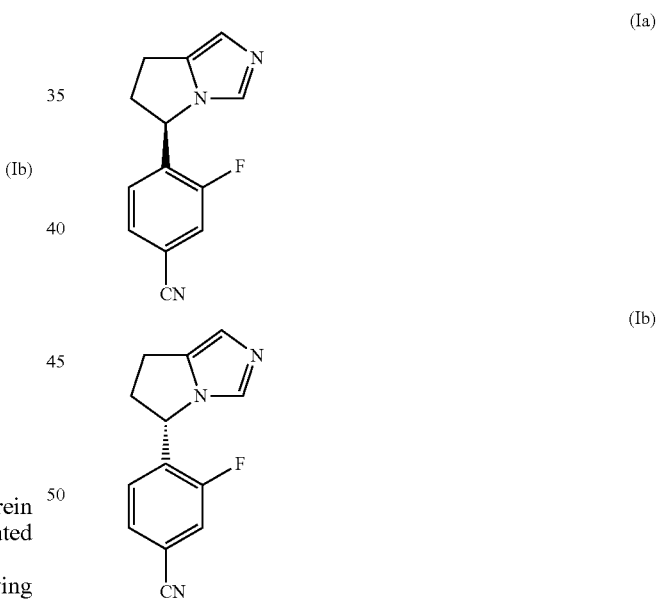
(Ia)

(Ib)

(iii) converting the compound of formula (Ia) or the compound of formula (Ib) to a pharmaceutically acceptable salt thereof.

10. The process according to claim 9, wherein the pharmaceutically acceptable salt is a monophosphate salt.

* * * * *